United States Patent [19]

Maurer et al.

[11] 3,962,147
[45] June 8, 1976

[54] PERFUME COMPOSITION CONTAINING 6,10 DIMETHYL - SPIRO [4.5]DECANE-TYPE COMPOUNDS

[75] Inventors: Bruno Maurer, Collonge-Bellerive; Michel G. Fracheboud; Günther Ohloff, both of Bernex-Geneva, all of Switzerland

[73] Assignee: Firmenich S.A., Geneva, Switzerland

[22] Filed: May 30, 1975

[21] Appl. No.: 582,265

Related U.S. Application Data

[62] Division of Ser. No. 363,187, May 23, 1973, Pat. No. 3,923,873.

[30] Foreign Application Priority Data

July 17, 1972 Luxemburg............................ 65737
May 29, 1972 Luxemburg............................ 65431

[52] U.S. Cl.............................. 252/522; 260/488 R; 260/586 G; 260/617 R; 426/538
[51] Int. Cl.²........................ C11B 9/00; A61K 7/46
[58] Field of Search.................. 252/522; 260/488 R

[56] References Cited
UNITED STATES PATENTS 3,880,888   4/1975   Demole.............................. 252/522
3,894,088   7/1975   Naegli................................ 252/522

OTHER PUBLICATIONS

P. C. Mukharji et al., Chem. and Indus. 1970, 553.
B. E. Ratcliffe et al., Synth. Comm. 2, 157 (1972).
James A. Marshall et al., J. Org. Chem. 35, 192 (1970).
James A. Marshall et al., J. Amer. Chem. Soc. 89, 2750 (1967).
E. Piers et al., J. Amer. Chem. Soc. 94, 2895 (1972).
James A. Marshall et al., Chem. Comm. 1968, 391.

*Primary Examiner*—Veronica O'Keefe
*Attorney, Agent, or Firm*—Pennie & Edmonds

[57] ABSTRACT

Use of bicyclic compounds, some of which are new, as perfuming and/or flavoring ingredients in the manufacture of perfumes and perfumed products and/or in the preparation of artificial flavors for foodstuffs, animal feeds, beverages, pharmaceutical preparations and tobacco products.

Process for the preparation of said bicyclic compounds.

1 Claim, No Drawings

PERFUME COMPOSITION CONTAINING 6,10 DIMETHYL - SPIRO [4.5]DECANE-TYPE COMPOUNDS

This is a division of application Ser. No. 363,187 filed May 23, 1973, now U.S. Pat. No. 3,923,873.

SUMMARY OF THE INVENTION

The invention relates to the use of a new class of valuable perfuming and/or flavouring ingredients. Said ingredients are bicyclic compounds of formula

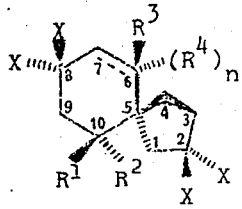

I containing a single or a double bond in the position indicated by the dotted line and wherein the index $n$ represents the integers zero or 1, one of the pairs of symbols X represents, when said symbols are taken together, an oxygen atom or, when said symbols are taken separately, a hydroxyl or an O-acyl group and a hydrogen atom, and the other pair represents two hydrogen atoms and wherein i. one of the symbols $R^1$ and $R^2$ represents a lower alkyl group and the other is a hydrogen atom and $R^3$ represents a lower alkyl group when the index n is zero; or ii. each of the symbols $R^1$, $R^2$, $R^3$ and $R^4$ represents a lower alkyl group or a hydrogen atom provided however that the pairs:

$R^1$ and $R^2$, and $R^3$ and $R^4$, respectively, cannot simultaneously comprise more than one alkyl group.

The invention also relates to new bicyclic compounds of formula

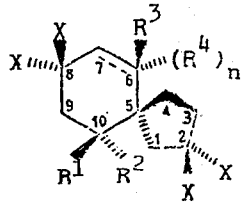

Ia wherein the pair of symbols X in position 8 is defined as in formula I and the other represents two hydrogen atoms and, wherein the position of the possible double bond, the index $n$ and the symbols $R^1$, $R^2$, $R^3$ and $R^4$ have the same meaning as for formula I; or wherein the pair of symbols X in position 2 represents a hydroxyl or an O-acyl group and a hydrogen atom, and the other represents two hydrogen atoms, and wherein the position of the possible double bond, the index $n$ and the symbols $R^1$, $R^2$, $R^3$ and $R^4$ are defined as indicated hereinabove.

The invention further relates to a process for the preparation of bicyclic compounds of formula I which comprises:

A. oxidizing a compound of formula

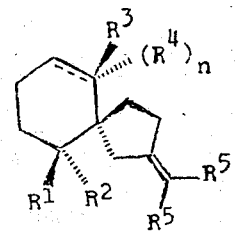

II wherein each of the symbols $R^5$ represents a lower alkyl group and wherein the position of the possible double bond, the symbols $R^1$, $R^2$, $R^3$ and $R^4$ and the index n have the same meaning as for formula I, by means of singlet oxygen and treating the thus obtained oxidation mixture with an acidic reagent, to afford a compound of formula I wherein the pair of symbols X in position 2 represents an oxygen atom and the other two hydrogen atoms; or B. oxidizing a compound of formula II as set forth under letter A by means of an oxidizing agent able to split the exocyclic double bond of the compound II to afford a compound of formula I as set forth under letter A; or C. reducing the ketone obtained under letter A or B to afford a compound of formula I wherein the pair of symbols X in position 2 represents a hydroxyl group and a hydrogen atom and the other represents two hydrogen atoms and wherein the index n and the symbols $R^1$, $R^2$, $R^3$ and $R^4$ are defined as indicated under letter A; or D. esterifying the alcohol obtained under letter C to afford a compound of formula I wherein the pair of symbols X in position 2 represents an O-acyl group and a hydrogen atom and the other represents two hydrogen atoms and wherein the index n and the symbols $R^1$, $R^2$, $R^3$ and $R^4$ are defined as indicated under letter C; or E. reducing a compound of formula I wherein the pair of symbols X in position 2 represents an oxygen atom and the other represents two hydrogen atoms and wherein the index n and the symbols $R^1$, $R^2$ and $R^3$ are defined as indicated under letter (i) by means of a reagent able to convert a ketonic function in a methylene group and oxidizing the thus obtained reduction mixture to afford a compound of formula I wherein the pair of symbols X in position 8 represents an oxygen atom and the other represents two hydrogen atoms and wherein the index $n$ and the symbols $R^1$, $R^2$ and $R^3$ are defined as indicated hereinabove; or F. oxidizing a compound of formula

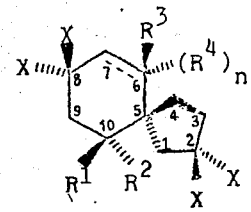

Ib wherein all symbols X represent a hydrogen atom and wherein the index n and the symbols $R^1$, $R^2$ and $R^3$ are defined as indicated under letter E to afford a compound of formula I as set forth under letter E; or G. reducing a compound of formula I wherein the pair of symbols X in position 8 represents an oxygen atom and the other represents two hydrogen atoms and wherein the index n and the symbols $R^1$, $R^2$, $R^3$ and $R^4$ are defined as for formula I to afford a compound of formula I wherein the pair of symbols X in position 8 represents a hydroxyl group and a hydrogen atom and the other represents two hydrogen atoms and wherein the index $n$ and the symbols $R^1$, $R^2$, $R^3$ and $R^4$ are defined as indicated hereinabove; or H. esterifying the alcohol obtained under letter G to afford a compound of formula I wherein the pair of symbols X represents an O-acyl group and a hydrogen atom and the other represents two hydrogen atoms and wherein the index $n$ and the symbols $R^1$, $R^2$, $R^3$ and $R^4$ are defined as indicated under letter G.

BACKGROUND OF THE INVENTION

One of the main objects of the aromatization of foodstuffs for instance is to restore the original quality and nature of the flavour, aroma and taste of a given foodstuff material. Very often in fact the organoleptic properties of foodstuffs particularly diminish or are somehow modified in the course of the processes of freezing and storage, or during the modifications, such as cooking or baking, to which the foodstuffs are subjected in order to yield an edible material.

In the past the aromatization was mainly achieved by using materials of natural origin. Nowadays, however, synthetic chemical compounds are used at an ever increasing rate. Said compounds possess the advantage of being available very often in unlimited quantities and at prices lower than those of the natural materials. Moreover, due to the fact that the flavouring character of a natural material is the result of the overall effect determined by the combination and interaction of each of its constituents, the effects achieved by said natural material are very often not as well reproducible as those obtained by the use of the pure synthetic compounds.

In the field of perfumery the man in the art has to solve a similar problem in attempting to reconstitute the olfactive notes of certain natural essential oils or extracts. The perfumer's creativity however is continually boosted by the finding of new synthetic compounds, the organoleptic properties of which will enable him to introduce unprecedented olfactive characters or nuances into new phantasy perfume compositions.

As a consequence, the problem that the chemical industry has to solve is to satisfy the increasing demand of organoleptically interesting chemicals in order to better suit the specific needs of flavourists and perfumers.

The compounds of formula I wherein one of the pairs of symbols $R^1$ and $R^2$ and $R^3$ and $R^4$, respectively, represents a methyl group and the other is a hydrogen atom possess a sesquiterpenoid skeleton containing 12 carbon atoms. Hitherto the use of these specific compounds as perfuming and/or flavouring ingredients has never been recognized in the art.

By means of an original, industrially and economically advantageous process of synthesis is now possible to put to the disposal of perfumers and flavourists a new class of valuable perfuming and flavouring ingredients.

PREFERRED EMBODIMENT OF THE INVENTION

In the definition of the above mentioned formulae, the term "lower alkyl group" is defined to mean a branched or linear alkyl group containing from 1 to 6 carbon atoms, as e.g. a methyl, ethyl, n-propyl, isopropyl, n-butyl, isobutyl or ter-butyl group.

We have now found that compounds of formula I possess interesting organoleptic properties and represent very useful ingredients for the preparation of perfumes or perfumed products, as well as for the reconstruction of essential oils. We have equally found that the said compounds are particularly appreciated in the preparation of various artificial flavours and for flavouring foodstuffs, animal feeds, beverages, pharmaceutical preparations and tobacco products.

In the perfumery the compounds of formula I can improve, enhance or modify various olfactive notes, e.g. woody, earthy or balsamic notes. By the use of the compounds of formula I, it is thus possible to create perfume compositions possessing a modern or more classical new fresh and woody character reminiscent in some instances of the odour of amber, ylang, sandelwood or patchouli for example. It was furthermore noticed that the thus improved or modified woody notes were, in some cases, particularly tenacious. The use of the said compounds is also appreciated for the manufacture of perfumed products as e.g. soaps, detergents, waxes, household materials or cosmetic preparations.

When the compounds of formula I are used as perfuming ingredients in perfume compositions the more interesting effects are achieved by the use of proportions comprised between about 0.5 and about 2 % of the total weight of the perfumed composition. Depending upon the desired effect or upon the nature of the other constituents of a given composition, lower, e.g. of the order of 0.01 %, or higher concentrations, from about 5 to 10 % (parts by weight), can also be used. When the said compounds are used as reinforcing ingredients in perfumed bases the concentrations used can be as high as about 80 % of the total weight of the said base.

The compounds of formula I are also appreciated in the flavour industry. Depending upon the nature of the products in which they are incorporated, the said compounds can improve, enhance or modify various gustative notes such as woody, slightly earthy or balsamic notes, in some instances reminiscent of these of fresh berries. They are particularly appreciated for the preparation of artificial flavours of walnuts, hazelnuts, peanuts or those of citrus fruits as e.g. lemon or grapefruit, or even those of bilberries or cranberries.

Owing to their specific organoleptic properties the said compounds can also be used for flavouring tobacco and tobacco products. For example, they can improve various woody or amber-like notes reminiscent in some instances of the taste of certain oriental tobaccos.

Depending upon the nature of the flavoured material or upon the desired effect, the proportions used can vary within wide limits and being of the order of 1 ppm to 1 % of the total weight of the flavoured material.

The more interesting effects can be achieved by the use of proportions comprised between about 50 and about 100 ppm of the total weight of the flavoured product.

When the said compounds are used as ingredients for the preparation of artificial flavours, they can be used in proportions comprised between about 0.1 and about 15 % of the total weight of the said flavouring composition, the proportions preferably used being of the order of 1 to 10 %.

Owing to the presence of various substituents in the positions 2, 6 and 10 or 6, 8 and 10 of the spiranic skeleton, more precisely defined as a spiro[4.5]decane skeleton, the formula I can represent several stereoisomeric forms of the given compound. As a consequence it is necessary to use a specific nomenclature in order to define these particular bicyclic derivatives. In the name "6,10 cis-dimethyl-(5rC$^1$)-spiro [4.5]dec-6-en-2-one", the term "(5rC$^1$)" means that the stereochemical orientation of one of the alkyl substituents is relative to the bond comprised between the carbon atom at position 5 and that at position 1 [see J. Org. Chem. 35, 194 (1970), footnote 16$^a$]: 6,10 cis-dimethyl-(5rC$^1$)-spiro[4.5]dec-6-en-2-one is a bicyclic ketone wherein the methyl group in position 10 possesses a cis-configuration relative to the said $C_5$-$C_1$ bond.

The alkyl substituents in position 6 or 10 can by all evidence possess a cis- or a trans- configuration relative to the said $C_5$-$C_1$ bond. Moreover, the possible hydroxyl or O-acyl group in position 8 may have an axial or an equatorial configuration. Equally, the possible hydroxyl or O-acyl group in position 2 can possess a cis- or trans- configuration relative to the $C_{10}$-$C_5$ bond. Therefore the said formula represents either an individual stereoisomer or any possible arrangement of the said stereoisomeric forms. Finally, owing to the presence of chirality centres in the positions 2,5,6 and 10 or 6, 8 and 10 of the bicyclic skeleton, the formula I is deemed to represent either meso, racemic or optically active compounds.

According to the invention the compounds of formula I can be used in a pure isomeric form. However, in some instances, owing to the fact that the gustative or olfactive effect of the given mixture is often similar to that of one of the pure stereoisomeric constituents, for practical and economical reasons, mixtures of stereoisomers as directly obtained by the process of the invention can also be used.

Among the compounds of formula I which can be used according to the invention the following are new compounds: (−) 6,10 cis-dimethyl-(5rC$^1$)-spiro[4.5]-dec-6-en-2-one, 6,10 cis or trans-dimethyl-(5rC$^1$)-spiro[4.5]dec-6-en-2-ol, 6,10 cis or trans-dimethyl-(5rC$^1$)-2-acetoxy-spiro[4.5]dec-6-ene, 6 cis, 10 cis or trans-dimethyl-(5rC$^1$)-spiro[4.5]decan-2-ol, 6 trans, 10 trans-dimethyl-(5rC$^1$)-spiro[4.5]decan-2-ol, 6 cis, 10 cis or trans-dimethyl-(5rC$^1$)-2-acetoxy-spiro[4.5]-decane, 6 trans, 10 trans-dimethyl-(5rC$^1$)-2-acetoxy-spiro[4.5]decane, 6,10 transdimethyl-(5rC$^1$)-spiro[4.5]dec-6-en-8-one, 6 cis or trans, 10 trans-dimethyl-(5rC$^1$)-spiro[4.5]decan-8-one, 6,10 trans-dimethyl-(5rC$^1$)-spiro[4.5]dec-6-en-8 -ol, 6 cis or trans, 10 transdimethyl-(5rC$^1$)-spiro[4.5]decan-8-ol, 6,10 trans-dimethyl-(5rC$^1$)-8-acetoxy-spiro[4.5]dec-6-ene and 6 cis or trans, 10 transdimethyl-(5rC$^1$)-spiro[4.5]decane.

Known compounds of formula I are a. 6,10 trans-dimethyl-(5rC$^1$)-spiro[4.5]dec-6-en-2-one: prepared from trans-6,10-dimethyl-bicyclo[4.4.0]deca-1,4-dien3-one according to a method described in J. Org. Chem. 35, 192 (1970). B.p.: 64°–66°C/0.05 Torr.

IR (neat) : 1740, 1450, 1408, 1380, 1160, 902 cm$^{-1}$
NMR (CCl$_4$) : 0.92 (3H, d, J=6.5 cps); 1.66 (3H, d, J=1.5 cps); 2.10 (2H, s); 5.37 (1H, m) δ ppm
MS : M$^+$ = 178; m/e = 107, 93, 44, 41.

b. 6 cis, 10 trans-dimethyl-(5rC$^1$)-spiro[4.5]decan-2-one: prepared by catalytic hydrogenation of the corresponding unsaturated ketone (see letter (a) according to the method cited under letter (a).

IR (neat) : 1740, 1410, 1382, 1254, 1110, 1070, 950 cm$^{-1}$
NMR (CCl$_4$) : 0.85 (3H, s, J=6 cps); 0.88 (3H, d, J=6 cps); 1.99 (2H, d, J=3 cps); 2.08 (2H, s) δ ppm
MS : M$^+$ = 180; m/e = 165, 138, 109, 95, 67, 55.

c. 6 trans, 10 trans-dimethyl-(5rC$^1$)-spiro[4.5]decan-2one: prepared as indicated under letter (b). m.p.: 21°–23°C.

IR (neat) : 1740, 1410, 1380, 1250, 1110, 1070, 950 cm$^{-1}$
NMR (CCl$_4$) : 0.87 (6H, d, J=5 cps); 2.13 (2H, s) δ ppm
MS : M$^+$ = 180; m/e = 165, 138, 109, 95, 67, 55.

d. (±) 6,10 cis-dimethyl-(5rC$^1$)-spiro[4.5]dec-6-en-2-one: prepared from 6,10 cis-dimethyl-(5rC$^1$)-2-methoxy-spiro[4.5] deca-1,6-diene according to a method described in Chem. Comm. 1970, 1232.

IR (neat) : 1740, 1450, 1408, 1380, 1160, 902, 805 cm$^{-1}$
NMR (CCl$_4$): 0.93 (3H, d, J=6 cps); 1,65 (3H, d, J=1.5 cps); 2.15 (2H, broad s); 5.40 (1H, m) δ ppm
MS : M$^+$ = 178; m/e = 107, 93, 44, 41.

e. 6 cis, 10 cis-dimethyl-(5rC$^1$)-spiro[4.5]decan-2-one: prepared from 6 cis, 10 cis-dimethyl-(5rC$^1$)-2-isopropylidenespiro[4.5]decane according to a method described in J. Am. Chem. Soc. 89, 2750 (1967). n$_D^{20}$ : 1.4891

IR (neat) : 1740, 1400, 1375, 1249, 1182, 1158, 1054, 940 cm$^{-1}$
NMR (CCl$_4$) : 0.85 (6H, d, J=6 cps); 1.91 (4H, s) δ ppm
MS : M$^+$ = 180; m/e = 165, 151, 138, 123, 109, 95, 82.

It has to be pointed out that, in the above cited references to the literature, the use of the said compounds as perfuming and/or flavouring ingredients has never been recognized.

As indicated above some of the compounds of formula I can be prepared by oxidizing compounds of formula II. The said process may formally be visualized as an oxidative splitting of the exocyclic double bond of the said compounds of formula II.

Such a splitting can be effected either according to the conventional methods used to split a carbon-carbon double bond [see e.g. L. F. Fieser and M. Fieser, "Reagents for Organic Chemistry", Vol. I, p. 773, John Wiley & Sons, New York, 1967], or by means of an alkali metal metaperiodate in the presence of a catalytic amount of osmium tetroxide [see e.g. op. cit., p. 812], or by means of a metal oxide such as $CrO_3$ or of an oxidized metal derivative such as an alkali metal chromate or permanganate in the presence of a strong mineral acid.

The splitting of the said exocyclic double bond can also be achieved by treating the compound of formula II with a peracid, hydrolizing the thus obtained epoxyde and subsequently oxidizing the obtained diol. Suitable organic peracids include performic, peracetic, trifluoroperacetic, perphthalic or m-chloroperbenzoic acid. The said peracid preferably reacts with the higher substituted double bond [see Organic Reactions 7, 378

(1953), J. Wiley & Sons, New York], i.e. the exocyclic double bond of the compound of formula II. The subsequent hydrolysis can be carried out in an acidic medium, e.g. in the presence of a strong mineral acid such as $H_2SO_4$ or HCl. The oxidation of the thus obtained diol may be effected by means of a strong oxidizing agent, e.g. lead tetraacetate or periodic acid [see e.g. L. F. Fieser and M. Fieser, "Reagents for Organic Chemistry", vol. I, p. 546 and 816, J. Wiley & Sons, New York, 1967].

According to another embodiment of the process of the invention the oxidative splitting of the exocyclic double bond of the compound of formula II can also be effected by means of singlet oxygen and subsequent treatment of the obtained oxidation mixture with an acidic reagent. Singlet oxygen can be generated by dye-sensitized photooxygenation. A dyestuff such a porphyrine, methylene blue, eosin, chlorophyl, Rose Bengal or xanthene is conveniently used [see e.g. Liebigs Ann. Chem. 674, 93 (1964); Angew. Chem. 69, 579 (1957)]. Said photooxygenation can be carried out at a temperature near to or lower than 0°C, and in the presence of an aqueous or organic medium. Suitable solvents include water, an aqueous organic solvent, an aromatic or aliphatic hydrocarbon such as e.g. benzene, toluene or n-hexane, an alcohol, e.g. methyl or ethyl alcohol, an ether such as e.g. dioxan or tetrahydrofuran, or a mixture of at least two of the above mentioned solvents. Equally, as acidic reagent Lewis acids can be conveniently used. For instance, a metalhalide such as $AlCl_3$, $ZnCl_2$, $SnCl_4$ or $FeCl_3$ can be employed. $BF_3$ is however preferred.

In accordance with the process of the invention it is now possible to advantageously convert 6,10 cis-dimethyl(5rC$^1$)-2-isopropylidene-spiro[4.5]dec-6-ene into 6,10 cis-dimethyl-(5rC$^1$)-spiro[4.5]dec-6-en-2-one. The bicyclic olefinic compound used as starting material in the above process can be obtained by reducing (—) β-vetivone according to the usual techniques, acylating the reduction mixture thus obtained and finally reducing the ester obtained by means of an alkali metal in liquid ammonia. The preparation of 6,10 cis-dimethyl(5rC$^1$)-spiro[4.5]dec-6-en-2-one as well as that of the starting material can be illustrated by the following reaction scheme:

possessing a ketone function in position 8 may be obtained by reducing a compound of formula I wherein the pair of symbols X in position 2 represents an oxygen atom and the other represents two hydrogen atoms and wherein the index $n$ and the symbols $R^1$, $R^2$ and $R^3$ are defined as indicated under letter (i) by means of a reagent able to convert a ketonic function in a methylene group and oxidizing the thus obtained reduction mixture.

The said reduction can be effected by means of a metal such as zinc, in the presence of a strong mineral acid such as hydrochloric acid for example. This reduction can also be effected by means of a reactant such as hydrazine, in the presence of a base such as an alkali metal hydroxide, and a polar solvent possessing a high boiling point such as e.g. ethylene glycol, according to the Huang-Minlon'method [see L. F. Fieser & M. Fieser, Reagents for Organic Chemistry, Vol. I, p. 435, John Wiley & Sons, New York, 1967]. The reduction of the above bicyclic ketones can moreover be effected via the corresponding tosylhydrazone, by means of an alkali metal hydride, alumiumhydrides or boronhydrides such as $NaBH_4$ for example [see Tetrahedron 22, 487 (1966)].

The oxidation of the thus obtained reaction mixture, as well as that of the bicyclic olefinic compound of formula Ib, may be effected by means of gazeous oxygen in the presence of a U.V. light source, or by means of a metal oxide such as e.g. $CrO_3$, in the presence of a strong mineral acid. An oxidizing agent such as terbutyl chromate or a $CrO_3$-pyridine complex may also be used [see J. Org. Chem. 34, 3587 (1969)].

The compounds of formula I which possess a cyclic double bond can be used as starting materials for the preparation of compounds having a saturated bicyclic skeleton. The said starting materials can be reduced according to the usual techniques. For example, catalytic hydrogenation of 6,10 cis-dimethyl-(5rC$^1$)-spiro[4.5]dec-6-en-2-one yields a mixture of 6 cis and trans, 10 cis-dimethyl-(5rC$^1$)-spiro[4.5]decan2-one. Moreover, the compounds of formula I wherein the symbols X are taken together and represent an oxygen atom can be converted into the corresponding hydroxy-derivatives. For example, by reducing 6,10 cis-dimethyl-(5rC$^1$)-spiro[4.5]dec-6-en-2-one with an al-

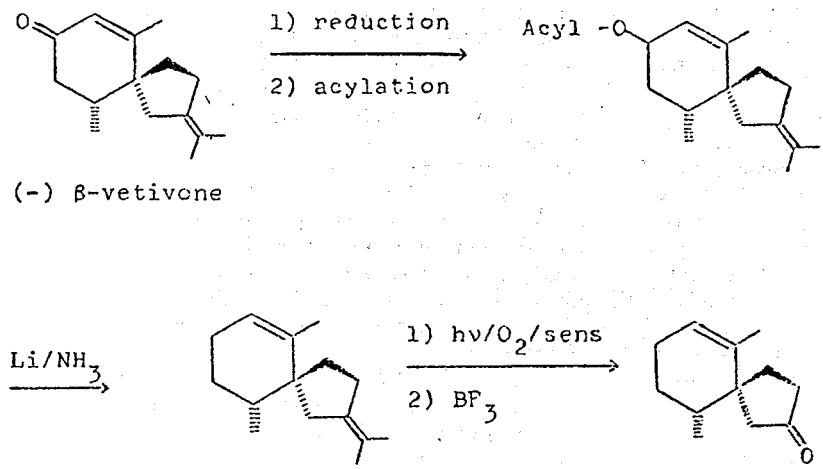

(−) β-vetivone

According to another embodiment of the process of the invention some of the compounds of formula I kali metal aluminiumhydride there is obtained 6,10 cis-dimethyl-(5rC$^1$)-spiro[4.5]dec-6-en-2-ol. By esterifying the thus obtained alcohols it is also possible to obtain the corresponding esters, e.g. the formates, the acetates, propionates or butyrates.

Finally, the compounds of formula I wherein one of the symbols X represents a hydroxyl group and the other is a hydrogen atom can be oxidized to afford the corresponding ketones. 6,10 trans-Dimethyl-($5rC^1$)-spiro[4.5]dec-6-en-2-one is thus obtained by oxidation of 6,10 trans-dimethyl-($5rC^1$)spiro[4.5]dec-6-en-2-ol by means of a reactant usually known in the art to convert a secondary alcohol into the corresponding ketone.

The invention is illustrated in a more detailed way by the following examples wherein the temperatures are given in degrees centigrades.

EXAMPLE 1

A base perfume composition of the Chypre type was prepared by admixing the following ingredients (parts by weight):

| | |
|---|---|
| α-Phenylethyl acetate | 30 |
| Undecenal 10%* | 100 |
| α-Methylundecenal 10%* | 20 |
| Coumarin | 60 |
| Vanillin | 5 |
| Musk ketone | 55 |
| Cyclopentadecanone 10%* | 30 |
| α-Isomethylionone | 60 |
| Absolute oak moss | 20 |
| Absolute labdanum | 10 |
| Synthetic galbanum | 10 |
| Synthetic castoreum | 20 |
| Methyl 2-pentyl-3-oxo-cyclopentyl-acetate | 50 |
| Benzyl acetate | 100 |
| Indol 10%* | 10 |
| Hexylcinnamic aldehyde | 50 |
| Synthetic rose | 50 |
| Patchouli | 20 |
| Synthetic bergamot | 200 |
| Total | 900 |

* in diethyl phthalate

By adding to 90 g of the above composition 10 g of a 10% solution of 6,10 cis-dimethyl-($5rC^1$)-spiro[4.5]-dec-6-en-2-one or of 6,10 trans-dimethyl-($5rC^1$)-8-acetoxy-spiro[4.5]dec-6-ene, in diethyl phthalate, there was obtained a new perfume composition possessing a very pleasant and original woody, in some instances slightly earth, character, having moreover a very natural richness.

By adding in the same proportions either one of the corresponding saturated ketones or esters or one of the corresponding saturated or unsaturated alcohols, there was obtained a perfume composition possessing a rich woody, amber-like note.

In most instances it was observed that the said woody note was very tenacious.

EXAMPLE 2

A base perfume composition for a masculine Eau de Cologne was prepared by admixing the following ingredients (parts by weight):

| | |
|---|---|
| Sage oil | 20 |
| Lavender oil | 150 |
| Synthetic bergamot | 200 |
| Lemon oil | 140 |
| Sweet orange oil | 40 |
| Synthetic galbanum 10%* | 20 |
| Muscone 10%* | 50 |
| Methyl 2-pentyl-3-oxo-cyclopentyl-acetate | 10 |
| 1,1-Dimethyl-6-ter-butyl-4-acetylindane | 10 |

| -continued | |
|---|---|
| α-Isomethylionone | 50 |
| Synthetic ylang | 80 |
| Synthetic jasmine | 25 |
| Synthetic geranium | 50 |
| Synthetic neroli | 100 |
| Coriander oil | 5 |
| Total | 950 |

* in diethyl phthalate

By adding to 95 g of the above base composition 5 g of a 10% solution of 6,10 cis-dimethyl-($5rC^1$)-spiro[4.5]dec-6-en-2-one or of 6,10 trans-dimethyl-($5rC^1$)-8-acetoxy-spiro[4.5]dec-6-ene, in diethyl phthalate, there was obtained a perfume composition possessing a novel and very distinct and tenacious woody odour.

By adding, in the same proportions, one of the corresponding saturated or unsaturated alcohols to the above base, there was obtained a new perfume composition possessing an agreeable, tenacious and slightly balsamic woody odour, reminiscent of that of cedar wood.

EXAMPLE 3

A base perfume composition for after-shave lotion was prepared by admixing the following ingredients (parts by weight):

| | |
|---|---|
| Menthol | 10 |
| Eugenol | 50 |
| Coumarin | 20 |
| Muscone 10%* | 20 |
| Phenylethyl alcohol | 120 |
| Lavender oil | 210 |
| Pimento oil | 40 |
| Cinnamon oil | 5 |
| Synthetic bergamot | 270 |
| Cyclopentadecanone 10%* | 30 |
| Methyl 2-pentyl-3-oxo-cyclopentyl-acetate | 20 |
| Absolute oak moss | 15 |
| Benzyl salicylate | 20 |
| Isobutyl salicylate | 30 |
| Geranium Bourbon oil | 70 |
| Musk ketone | 20 |
| Total | 950 |

*in 95% ethyl alcohol

By adding to 95 g of the above base composition 5 g of a 10% ethanolic solution of 6,10 cis-dimethyl-($5rC^1$)-spiro[4.5]dec-6-en-2-one, 6,10 trans-dimethyl-($5rC^1$)-spiro[4.5]dec-6-en-2-ol or 6,10 trans-dimethyl-8-acetoxy-spiro[4.5]dec-6-ene, there was obtained a new perfume composition possessing a vigourous woody and slightly spicy character. Moreover the said woody note, reminiscent of that of certain exotic woods, was particularly tenacious and powerful.

EXAMPLE 4

A base flavouring composition of the Tutti-Frutti type was prepared by admixing the following ingredients (parts by weight):

| | |
|---|---|
| Vanillin | 25 |
| Allyl caproate | 10 |
| Citral | 15 |
| Amyl butyrate | 35 |
| Sweet orange oil | 50 |
| Ethyl butyrate | 75 |
| Ethyl acetate | 150 |
| Amyl acetate | 150 |
| Lemon oil | 250 |
| Orange terpenes | 240 |
| Total | 1000 |

Two flavouring compositions were then prepared as indicated below (parts by weight):

| | A (test) | B (control) |
|---|---|---|
| Base composition | 100 | 100 |
| 6,10 cis-Dimethyl-(5rC$^1$)-spiro[4.5]dec-6-en-2-one | 100 | — |
| 95% Ethyl alcohol | 800 | 900 |
| Total | 1000 | 1000 |

Both mixtures A and B were then used for the preparation of the following foodstuffs, in the proportions of 100 g of flavouring composition per 100 kg of foodstuff.

Ice-cream: An ice-cream mixture was prepared from 1 liter of milk, 5 egg yolks and 250 g of sugar in the following manner: the milk was heated, the sugar and the egg yolks were mixed and the hot milk was added to the mixture while stirring. Stirring was continued until the mass thickened, and the flavour was added. The mixture was then frozen in the usual manner.

Pudding: A mixture of 60 g of sugar and 3 g of pectine was added to 500 ml of hot milk, while stirring. The mixture was brought to the boil for a few seconds, the flavour was added and the mixture allowed to cool.

The foodstuffs prepared as described above were then tasted by a panel of flavour experts who declared that the "test" foodstuffs possessed a more pronounced, well rounded and slightly woody fruity taste as compared with the "control" foodstuffs, reminiscent moreover of that of fresh bilberries or cranberries.

By substituting, in the same proportions, the above ketone by 6,10 cis-dimethyl-(5rC$^1$)-spiro[4.5]dec-6-en-2-ol or 6 cis, 10 cisdimethyl-(5rC$^1$)-spiro[4.5]decan-2-one, a similar effect was observed. The fruity and woody note possessed moreover a more marked green character.

EXAMPLE 5

A commercial bilberries jam was flavoured with a 10% ethanolic solution of 6,10 cis-dimethyl-(5rC$^1$)-spiro[4.5]dec-6-en-3-one, in the proportions of 10 ml of said ethanolic solution per 100 kg of flavoured material. The thus flavoured foodstuff was then compared by a panel of flavour experts with an unflavoured jam containing ethyl alcohol in the above given proportions. It was declared that the flavoured jam possessed a woody, slightly balsamic taste reminiscent of that of fresh bilberries.

EXAMPLE 6

To 1 litre of an acidulous sugar syrup (prepared by diluting 650 g of sucrose and 10 ml of a 50% aqueous solution of citric acid in 1000 ml of water), flavoured with lemon or grapefruit oil in the proportion of 30 g of the said oil per 100 l of syrup, there was added 1 ml of a 1% ethanolic solution of 6,10 cis-dimethyl(5rC$^1$)-spiro[4.5]dec-6-en-2-one. The thus flavoured beverage was then compared with an unflavoured syrup by a panel of flavour experts. These latter declared that the flavoured syrup as compared with the unflavoured one, possessed a more marked and very pleasant fruity taste with a slightly woody character.

By substituting, in the above beverage, 6,10 cis-dimethyl(5rC$^1$)-spiro[4.5]dec-6-en-2-one by the corresponding unsaturated alcohol, a similar effect was observed. In this latter case moreover the observed taste was slightly green.

EXAMPLE 7

7 g of a 1% ethanolic solution of 6,10 cis-dimethyl-(5rC$^1$)spiro[4.5]dec-6-en2-one were sprayed onto 100 g of an "american blend" tobacco mixture. The tobacco thus flavoured was used for the manufacture of test cigarettes, the smoke of which was then subjected to organic evaluation by comparison with unflavoured control cigarettes. The tobacco used to prepare the control cigarettes was preliminary treated with a corresponding amount of ethyl alcohol.

A panel of flavour experts defined the taste of the smoke of the test cigarettes as being more rounded than that of the control cigarettes, the said smoke possessing moreover a more marked woody character.

By following the same flavouring procedure, the panel of experts declared that the smoke of the test cigarettes flavoured by 6,10 cis-dimethyl-(5rC$^1$)-spiro[4.5]dec-6-en2-ol or 6,10 trans-dimethyl(5rC$^1$)-8-acetoxy-spiro[4.5]dec-6-ene possessed a more intense woody taste reminiscent of that of cedar wood and, in some instances, of the taste of certain oriental tobaccos.

EXAMPLE 8

6,10-Dimethyl-cis-(5rC$^1$)-spiro[4.5]dec-6-en-2-one

A solution of 10.0 g (49 mM) of a 1:1 mixture of cis 1,10-dimethyl-3-isopropylidene-bicyclo[4.4.0]dec-6-ene and 6,10cis-dimethyl-(5rC$^1$)-2-isopropylidene-spiro[4.5]dec-6-ene in 100 ml of a 1:1 mixture of benzene and methanol, was irradiated during 2 hr at 20° in the presence of gaseous oxygen, 50 mg of Rose Bengal and 50 mg of hydroquinone by means of a mercury vapour lamp, type Philips HPK-125W. After 35 min the absorption of oxygen ended (1225 ml). After evaporation of the volatile fractions, the obtained residue was dissolved in 100 ml ether and 15 ml of a 48 % ethereal solution of BF$_3$ was added thereto. 1 hr after complete addition, the reaction mixture has been taken up by water, extracted with ether and the combined organic phases treated according to the usual techniques to yield 7.6 g of a residue, which, upon purification by column chromatography on 150 g of neutral Al$_2$O$_3$ (activity II) gave 5.7 g of a material containing 50 % of the desired compound. The elution was first achieved by 500 ml of n-hexane followed by 350 ml of a 7:3 mixture of n-hexane - ethyl acetate.

The isolation of the pure compound was achieved as follows: the mixture as directly obtained by chromatography was refluxed for 90 min. in the presence of 5.70 g of the Girard-T reagent in 100 ml ethanol and 2 ml glacial acetic acid. After cooling, the reaction mixture was concentrated under vacuum, whereupon 100 ml of water containing 1.5 g of NaOH were added and the whole extracted with ether. The organic phase was then washed with an excess of concentrated HCl and the aqueous phase left at room temperature during 90 min. After extraction with ether, washing, drying and evaporation there were obtained on distillation 2.7 g (yield 70 %) of the desired bicyclic ketone.

B.p. 130°/16 Torr; $n_D^{20}$ = 1.5096

$[\alpha]_D^{20}$ = −42.20° (neat)

IR (neat) : 1740, 1670, 800, 780 cm$^{-1}$

NMR (CCl$_4$) : 0.90 (3H, d, J=6.5 cps); 1.64 (3H, d, J=1.5cps); 5.3 (1H, m) δ ppm MS :M$^+$ = m/e: 163, 150, 136, 122, 107, 93, 79, 79, 68.

The mixture of isomeric bicyclic hydrocarbons, used as starting material for the hereinabove preparation, was prepared as follows:

A solution of 21.8 g (100 mM) of a 1:1 mixture of α- and β- vetivone, which was isolated from Bourbon Vetiver oil according to Helv. Chim. acta 22, 640 (1939), in 100 ml of dry ether, was added under stirring to a suspension of 1.5 g (40 mM) of $LiAlH_4$ in 200 ml of dry ether. The addition was effected dropwise at such a rate as to keep the solvent to the boiling. After 12 additional hours stirring, the mixture was hydrolysed by means of 20 ml of a 10 % aqueous NaOH solution, whereupon it was filtered by taking care to wash the solide cake with ether. The combined organic phase was treated according to the usual techniques to yield 21.0 g of a raw mixture of the isomeric allylic alcohols. These latter were acetylated by reacting them with 60 ml of acetic anhydride and 150 ml of pyridine at room temperature and overnight. The volatile portions were taken off at reduced pressure and the residue diluted with 200 ml of 2N $H_2SO_4$. By extraction with ether followed by the usual treatment. 23.5 g of the mixture of raw isomeric unsaturated acetates were obtained.

This mixture was dissolved in 300 ml of dry ether and added dropwise to a solution of 4.23 g (604 m-atome-g) of lithium in 1400 ml of liquid ammonia, whereupon the whole was left at room temperature during 2 hr while refluxing. Solid $NH_4Cl$ (ca. 35 g) was then added until disappearance of the blue colour and the excess ammonia was finally taken off.

The thus obtained residue was taken up by a 1:1 mixture of ether and water, the organic phase was evaporated to dryness and the product obtained purified by means of column chromatography (500 g of neutral $Al_2O_3$; activity II). An elution with n-hexane gave 10.0 g of a 1:1 mixture of the isomeric bicyclic hydrocarbons.

EXAMPLE 9

6,10-cis-Dimethyl-($5rC^1$)-spiro[4.5]dec-6-en-2-ol

A solution of 1.0 g (5.6 mM) of 6,10-cis-dimethyl($5rC^1$)-spiro[4.5]dec-6-en-2-one in 10 ml dry ether was added dropwise and at room temperature to a suspension of 75 mg (2 m-atom-g) of $LiAlH_4$ in 50 ml of dry ether. The reaction mixture was then heated to reflux during 2 hr whereupon a 1:1 mixture of methanol and water was added thereto. After filtration and evaporation of the separated organic phase, there were collected 920 mg (ca. 90 %) of a raw material which, upon purification by column chromatography on silica gel (eluant: $CH_2Cl_2$) gave a product which was finally subjected to a distillation in a bulb tube apparatus to afford 400 mg (40 %) of the pure desired product.
B.p. 120°–125°/0.1 Torr; $N_D^{20}$ : 1.5181
$[\alpha]_D^{20}$ ; –4.9° (pure liquid)
IR (neat) : 3330, 1660, 845, 800 $cm^{-1}$
NMR ($CCl_4$): 0.92 (3H, d, J=6.5 cps); 1.62 (3H, d, J=1.5 cps); 1.72 (3H, broad s); 5.25 (1H, broad s) δppm
MS :$M^+$ = 180; m/e = 162, 147, 133, 120, 107, 93, 79, 67, 55.

EXAMPLE 10

6,10-Dimethyl-trans-($5rC^1$) -spiro[4.5]dec-6-en-2-ol

A solution of 2.8 g (ca. 16 mM) of 6,10-trans-dimethyl - ($5rC^1$)-spiro[4.5]deca-3,6-dien-2-one in 50 ml of anhydrous tetrahydrofuran was added to a solution of 65 ml of terbutanol in ca. 250 ml of liquid ammonia. To this mixture cooled to –37°, there were added by small portions and under stirring 3.03 g (437 m-atom-g) of lithium and the stirring was carried on until complete discolouration (ca. 4 hr). After evaporation of the excess ammonia, the obtained residue was taken up by a 1:1 mixture of ether and water. The organic phase gave by the usual techniques of washing, drying and evaporation 2.95 g of a raw product which, upon purification by column chromatography on silica gel (eluant: n-hexane/ethyl acetate 9:1) followed by fractional distillation under reduced pressure (0.01 Torr), gave 1.6 g (57 %) of the desired product.
IR (neat) : 3330, 1660, 845, 800 $cm^{-1}$
NMR ($CCl_4$) : 0.87 (3H, d, J=6 cps); 1.62 (3H, s); 4.22 (1H, m); 4.60 (1H, broad s); 5.24 (1H, m) δ ppm
MS : $M^+$ = 180; m/e = 147, 107, 105, 93.

EXAMPLE 11

6,10-trans-Dimethyl-($5rC^1$)-spiro[4.5]dec-6-en-2-one 2.8 g (28 mM) of $CrO_3$ have been added to a solution of 4.5 ml of pyridine in 65 ml of $CH_2Cl_2$, whereupon 0.85 g (ca. 4.7 mM) of 6,10-trans-dimethyl-($5rC^1$)-spiro[4.5]dec-6-en-2-ol in 7 ml of $CH_2Cl_2$ were slowly added thereto under stirring and at room temperature and finally left 1 hr at this temperature. The reaction mixture was then poured onto ice and extracted with n-pentane. The organic phase was subjected to the usual treatments of washing, drying and evaporation to afford 770 mg of raw material which, upon purification by column chromatography on silica gel (eluant: 95:5 n-hexane:ethyl acetate) and distillation under vacuum (0.05 Torr) in a bulb apparatus gave 600 mg (ca. 75 %) of the desired product. This compound was identical in all respects to that described in the literature [J. Org. Chem. 35, 192 (1970)].

EXAMPLE 12

6 cis, 10 cis-Dimethyl-($5rC^1$)-spiro[4.5]decan-2-ol

This alcohol was obtained by reduction of 6 cis, 10 cis-($5rC^1$)-spiro[4.5]decan-2-one according to the method described in Example 9.
Mp. 60°–61°.
IR (KBr) : 3240, 1470, 1460, 1380, 1065, 1020, 940 $cm^{-1}$
NMR ($CCl_4$) : 0.95 (6H, d, J=6.5 cps); 4.07 (1H, m); 4.25 (1H, s) δ ppm
MS : $M^+$ = 182; m/e: 169, 135, 121, 107, 94, 83, 67.

EXAMPLE 13

6 cis, 10 cis-Dimethyl-($5rC^1$)-spiro[4.5]decan-2-one

A solution of 10.0 g (49 mM) of a 1:1 mixture of cis-1,10-dimethyl-3-isopropylidene-trans-bicyclo[4.4.0]decane and 6 cis, 10 cis-dimethyl-($5rC^1$)-2-isopropylidene-spiro[4.5] decane in 100 ml of a 1:1 mixture of benzene and methanol was treated as described in Example 8.

The mixture of the bicyclic ketones thus obtained was subjected to column chromatography on silica gel (0.05–0.2mm; eluant: hexane - benzene - ethyl acetate 85:5:10) to isolate cis-1,10-dimethyl-trans-bicyclo[4.4.0]decan-3-one with ca 35 % by weight yield (relative to the mixture of the hydrocarbons used).
M.P. 44–45° $[\alpha]_D^{20}$ = –67.5° (10 % in $CHCl_3$)
IR ($CHCl_3$) : 1710 $cm^{-1}$ NMR (CCl$_4$) : 0.63 (3H, s); 0.78 (3H, d, J=6 cps) δ ppm
MS : M$^+$ = 180; m/e: 165, 147, 138, 122, 95, 82, 69.

By further elution there was obtained with a 45 % yield the desired bicyclic ketone. The product thus obtained was identical in all respects to that described in the literature [see: J. Am. Chem. Soc. 89, 2750 (1967)].

The isomeric saturated hydrocarbons used as starting materials in the hereinabove preparation were synthesized as follows:

A solution of 25.0 g (115 mM) of a 1:1 mixture of α- and β-vetivone (see Example 8) in 500 ml ethanol, was subjected to hydrogenation in the presence of 10 % palladium on charcoal and 0.5 g of KOH. After filtration and evaporation of the clear filtrate there were obtained 21.5 g (ca. 85 %) of 1:1 mixture of the saturated bicyclic ketones. These compounds were then converted into their tosylhydrazone derivatives, according to Tetrahedron 22, 487 (1966), and these latter reduced by means of NaBH$_4$ in ethanol to afford 15.0 g (ca. 75 %) of the mixture of the isomeric bicyclic hydrocarbons.

EXAMPLE 14

6,10 trans-Dimethyl-(5rC$^1$)-spiro[4.5]dec-6-en-8-one

The title compound was synthesized by oxidizing a 7:3 mixture of 6,10 trans-dimethyl-(5rC$^1$)-spiro[4.5]-dec-6-ene and 6-methylene-10 trans-methyl-(5rC$^1$)-spiro[4.5]decane by means of ter-butyl-chromate in methylene chloride (yield 56 % based on the decane starting material).

IR (neat) : 3010, 1670, 1615, 1380, 1140 and 1182 cm$^{-1}$
NMR (CCl$_4$) : 0.95 (3H, d, J=6.5 cps); 1.89 (3H, d, J=1.5 cps); 5.58 (1H, q, J=1.5 cps) δ ppm
MS : M$^+$ = 178 (40); m/e: 136 (100); 121 (42); 108 (87); 107 (43).

The mixture used as starting material in the hereinabove process can be prepared as follows:

10-methyl-spiro[4.5]decan-6-one was alkylated by means of methyl-magnesium iodide under the reaction conditions commonly used in a Grignard reaction. 6,10-dimethyl-spiro[4.5]-decan-6-ol was thus obtained with an yield of 82 %.

IR (neat) : 3610, 3470, 1460, 1375, 1120, 1075, 935 and 910 cm$^{-1}$
NMR (CCl$_4$) : 0.80 (3H, d, J=6 cps); 1.14 (3H, d) δ ppm
MS : M$^+$ = 182 (16); m/e: 108 (59); 71 (100); 67 (65) 43 (99).

The obtained tertiary alcohol was then dehydrated by means of POCl$_3$ in pyridine to give a 7:3 mixture of 6,10 transdimethyl-(5rC$^1$)-spiro[4.5]dec-6-ene and 6-methylene-10 transmethyl-(5rC$^1$)-spiro[4.5]decane. These latter were separated one from the other by means of preparative vapour phase chromatography:

A
IR (neat) : 3050, 1650, 1450 and 1375 cm$^{-1}$
NMR (CDCl$_3$): 0.89 (3H, d,J= 6.5 cps); 1.96 (2H, m); 5.32 (1H, m) δ ppm;
MS : M$^+$ = 164 (46); m/e: 149 (74); 122 (76); 107 (100); 93 (76).

B
IR (neat) : 3100, 1635, 1445, 1375, 890 cm$^{-1}$
NMR (CDCl$_3$) : 0.85 (3H, d, J=7.5 cps); 4.78 and 4.67 (2H, 2m) δ ppm
MS : M$^+$ = 164 (23); m/e: 149 (84); 95 (96); 82 (83); 67 (100).

EXAMPLE 15

6 trans, 10 trans-Dimethyl-(5rC$^1$)-spiro[4.5]decan-8-one

By hydrogenation of the unsaturated ketone derivative, prepared in accordance with the procedure described in Example 14, in the presence of palladium on charcoal and KOH (see the method given in Example 13) there were obtained in approximately 100 % yield the desired product.

M.p. 41°–2°.
IR (neat) : 1720, 1475, 1380, 1340, 1280, 1140 and 540 cm$^{-1}$
NMR (CCl$_4$) : 0.93 (6H, 2d, J= 6 cps) δ ppm
MS : M$^+$ = 180 (30); m/e: 109 (74); 95 (100); 71 (62); 67 (93).

By reducing according to the same procedure 6,10 trans-dimethyl-(5rC$^1$)-spiro[4.5]dec-6-en-8-one by means of lithium in liquid ammonia (see Example 8), there was obtained a 6:4 mixture of 6 trans, 10 trans-dimethyl-(5rC$^1$)-spiro[4.5]decan-8-one, respectively.

EXAMPLE 16

6 trans, 10 trans-Dimethyl-(5rC$^1$)-spiro[4.5]decan-8-ol

By reducing the corresponding ketone derivative, obtained according to the procedure described in Example 15, by means of LiAlH$_4$ (see Example 9), there was obtained a mixture which, upon separation by vapour phase chromatography yielded 2 epimeric alcohols (A and B). in the ratio 8:2, respectively.

A
M.p. 52°–4°.
IR (CCl$_4$) : 3620, 3340, 1375, 1115, 1030 cm$^{-1}$
NMR (CCl$_4$) : 0.87 (6H, 2d, J=6 cps); 3.48 (1H, m); 3.60 (1H, broad s) δ ppm
MS : M$^+$ = 182 (14); m/e: 110 (71); 96 (89); 95 (81); 67 (100).

B
M.p. 103°–104°
IR (CCl$_4$) : 3630, 3360, 1380, 1025, 1015, 945 cm$^{-1}$
NMR (CCl$_4$) : 0.80 (6H, 2d, J=6 cps); 3.28 (1H, s); 3.89 (1H, m) δ ppm
MS : M$^+$ = 182 (2); m/e: 96 (88); 95 (86); 67 (100); 55 (71).

Isomer B, which possesses the OH function in the equatorial position, was equally synthetized in its pure state by reduction of the corresponding ketone, prepared according to Example 15, by means of IrCl$_4$ [see: L. F. Fieser and M. Fieser, "Reagents for Organic Chemistry", John Wiley & Sons, New York, 1967]; yield 71 %.

EXAMPLE 17

6 trans, 10 trans-Dimethyl-(5rC$^1$)-8-acetoxy-spiro[4.5]decane

The isomeric alcohols prepared according to Example 16 were esterified by means of acetic anhydride in pyridine in order to give the desired esters.

A (axial ester function) yield 75 %
IR (neat) : 1735, 1360, 1240, 1025 cm$^{-1}$
NMR (CCl$_4$) : 0.87 (6H, 2d, J=6 cps); 1.89 (3H, s); 4.60 (1H, m) δ ppm
MS : m/e: 96 (97); 95 (69); 67 (74); 43 (100).

B (equatorial ester function) yield 90 %

IR (neat) : 1735, 1375, 1245, 1140, 1020, 945 cm$^{-1}$
NMR (CCl$_4$) : 0.83 (6H, 2d, J=6 cps); 1.95 (3H, s); 4.89 (1H, m) δ ppm
MS : m/e: 96 (100); 95 (67); 67 (76); 43 (99).

EXAMPLE 18

6,10 trans-Dimethyl-(5rC$^1$)-spiro[4.5]dec-6-en-8-ol

Starting from 6,10 trans-dimethyl-(5rC$^1$)-spiro[4.5]-dec-6-en-8-one (see Example 14) there was obtained the title compound by means of LiAlH$_4$ (see Example 9) with a yield of 95 %.

IR (neat) : 3340, 1650, 1370, 1140, 1030, 995 cm$^{-1}$
NMR (CCl$_4$) : 0.93 (3H, d, J=6.5 cps); 3.60 (1H, broad s); 4.05 (1H, broad s); 5.22 (1H, m) δ ppm
MS : M$^+$ = 180 (12); m/e: 105 (46); 85 (80); 84 (100); 67 (58).

EXAMPLE 19

6,10 trans-Dimethyl-(5rC$^1$)-8-acetoxy-spiro[4.5]dec-6-ene

The unsaturated alcohol obtained according to Example 18 was esterified by means of acetic anhydride in pyridine in order to give the title compound in 85 % yield.

IR (neat) : 1735, 1650, 1375, 1240, 1145, 1020 and 960 cm$^{-1}$
NMR (CCl$_4$) : 0.95 (3H, d, J=6.5 cps); 1.68 (3H, s); 1.90 (3H, s); 5.25 (2H, broad s) δ ppm
MS : m/e: 147 (89); 144 (81); 121 (93); 105 (100).

We claim:

1. A perfume composition which comprises at least one of the compounds of the formula

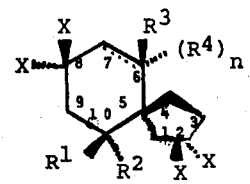

containing a single or a double bond in the position indicated by the dotted line and wherein the index $n$ represents the intergers zero or 1, one of the pairs of symbols $X$ represents when said symbols are taken together, an oxygen atom or, when said symbols are taken separately, a hydroxyl or an O-acyl group and a hydrogen atom, and the other pair represents two hydrogen atoms and wherein
  i. one of the symbols R$^1$ and R$^2$ represents a lower alkyl group and the other is a hydrogen atom and R$^3$ represents a lower alkyl group when the index $n$ is zero; or
  ii. each of the symbols R$^1$, R$^2$, R$^3$ and R$^4$ represents a lower alkyl group or a hydrogen atom provided however that the pairs
    R$^1$ and R$^2$, and
    R$^3$ and R$^4$, respectively,
cannot simultaneously comprise more than one alkyl group, and an inert diluent or a carrier.

* * * * *

UNITED STATES PATENT AND TRADEMARK OFFICE
CERTIFICATE OF CORRECTION

PATENT NO. : 3,962,147
DATED : June 8, 1976
INVENTOR(S) : Bruno Maurer et al.

It is certified that error appears in the above-identified patent and that said Letters Patent are hereby corrected as shown below:

Column 5, lines 39-40 "... gustative of olfactive..." should be --gustative or olfactive--

Column 5, lines 55,59 and 61 "transdimethyl" should be --trans-dimethyl--

Column 5, line 66 "4-dien3" should be --4-dien-3--

Column 6, lines 14-15 "decan-2one" should be --decan-2-one--

Column 8, line 17 "Huang-Minlon'method" should be --Huang-Minlon's method--

Column 8, line 40 "decan2" should be --decan-2--

Column 9, line 46 "earth" should be --earthy--

Column 11, line 34 "cisdimethyl" should be --cis-dimethyl--

Column 12, line 4 "en2-one" should be --en-2-one--

Column 12, lines 7,13 and 17 "test" should be --"test"--

Column 12, lines 9, 10 and 14 "control" should be --"control"--

Column 12, line 20 "en2-ol" should be --en-2-ol--

Column 12, line 31 "6,10cis" should be --6,10-cis--

UNITED STATES PATENT AND TRADEMARK OFFICE
CERTIFICATE OF CORRECTION

PATENT NO. : 3,962,147
DATED : June 8, 1976
INVENTOR(S) : Bruno Maurer et al.

It is certified that error appears in the above-identified patent and that said Letters Patent are hereby corrected as shown below:

Column 12, line 68 "MS:M$^+$ = m/e: 163, 150, 136, 122, 107, 93, 79, 79, 68." should be -- MS:M$^+$ = 178; m/e: 163, 150, 136, 122, 107, 93, 79, 68.--

Column 15, line 32 "decane" should be --decene--

Column 15, line 55 "transdimethyl" should be --trans-dimethyl--

Column 15, line 56 "transmethyl" should be --trans-methyl--

Signed and Sealed this

Twenty-sixth Day of October 1976

[SEAL]

Attest:

RUTH C. MASON
Attesting Officer

C. MARSHALL DANN
Commissioner of Patents and Trademarks